Dec. 29, 1942. J. J. GRULLEMANS Plant Pat. 563
KNIPHOFIA OR TRITOMA
Filed Aug. 22, 1942
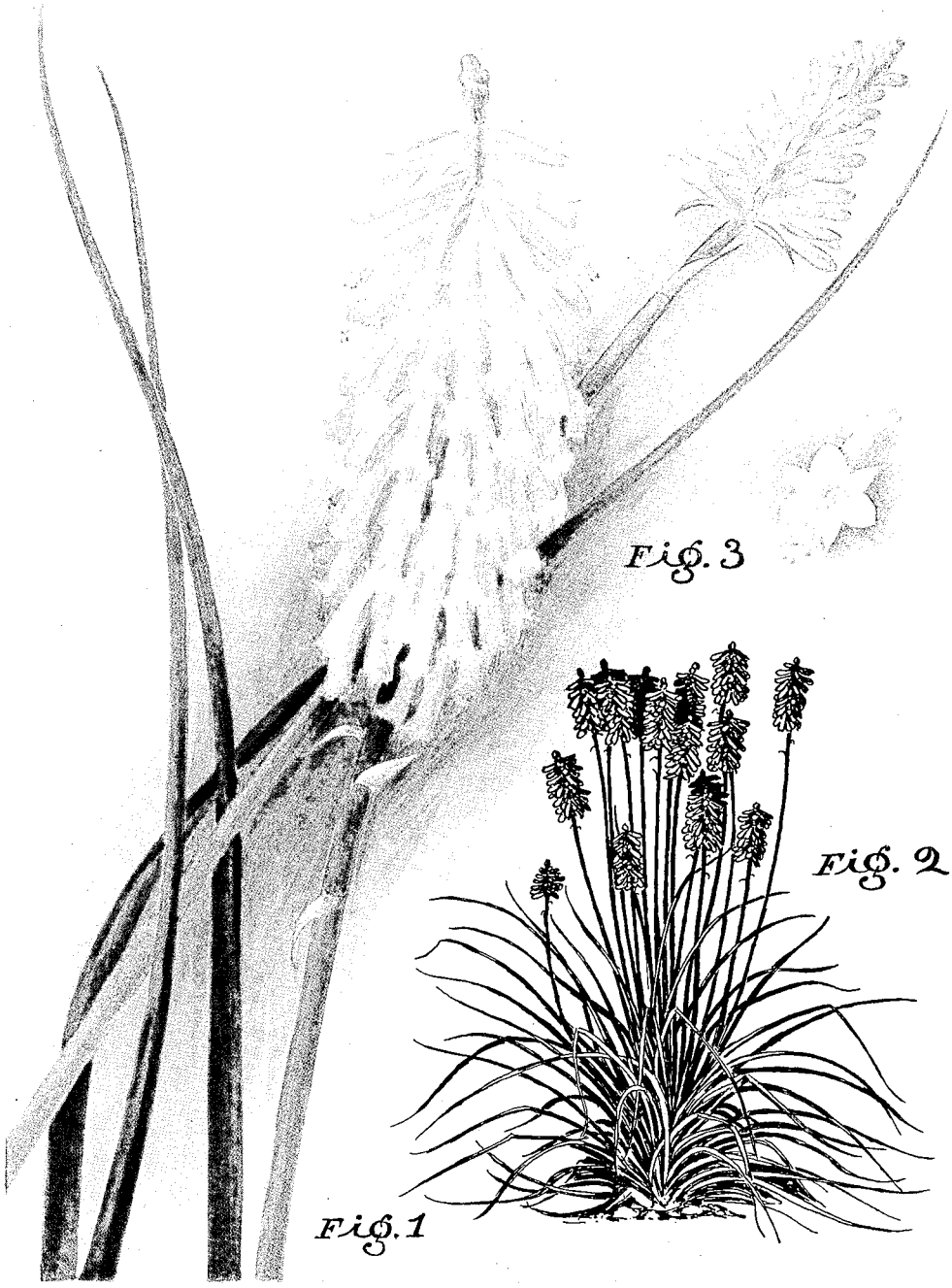
WITNESS
Addison E. Avery
INVENTOR.
John J. Grullemans,
by: John Harrow Bromard,
his attorney.

Patented Dec. 29, 1942

Plant Pat. 563

UNITED STATES PATENT OFFICE

563

KNIPHOFIA OR TRITOMA

John J. Grullemans, Painesville, Ohio, assignor to The Wayside Gardens Company, Mentor, Ohio, a corporation of Ohio Application August 22, 1942, Serial No. 455,742

1 Claim. (Cl. 47—60)

This invention relates to a new and distinct variety of Kniphofia, commonly termed Tritoma.

The cross pollination of plants by hand is necessarily a tedious and time-consuming operation and can be performed only during a very short interval when a number of favorable conditions of the blossoms exit concurrently. Consequently, the practice of seeking to obtain new varieties by allowing natural cross pollination is employed often. This practice consists of planting specimens of two different plants to be crossed in contiguous beds, or interpersed in the same bed with each other, depending upon the usual transfer of pollen by insects and wind to effect the cross pollination and the favorable aspect of the law of probabilities resulting from the relative proximity of the specimens to cross the particular specimens so planted. The characteristics of the resultant hybrids generally reflects their ancestry.

The present Kniphofia variety was the result of this type of cross pollination, the two plants thus crossed being the species *Kniphofia rufa* and the variety *Kniphofia uvaria grandiflora*. These plants were allowed to produce seed which was not gathered but allowed to fall in the bed and the bed was subsequently observed for desirable specimens. One such specimen was the present Kniphofia variety which partakes of outstanding characteristics of both parents, but which of the two parents was the seed parent and which the pollen parent is unknown.

The plant was first produced and discovered about 1934 and was first asexually reproduced in 1938 in the fields of The Wayside Gardens Company at Mentor, Lake County, Ohio, where the original plant was produced. Asexual reproduction by division has been carried on continuously since and the plant has reproduced true to form consistently.

The plant has the usual thin clustered roots of fleshy consistency and is relatively deep rooted. The roots are small and of very limited lateral spread. They generally are exceptionally hardy and free from disease and resistant to wetness and drouth. Their winter resistance is exceptional and they withstand the winters of northern Ohio without protection. The plant is relatively indifferent as to soil but it prefers a southern exposure in the sun with well drained soil.

The new variety is illustrated in the drawing in which Fig. 1 shows specimens of the stalks, flower spikes and leaves; Fig. 2 is a pen sketch on a reduced scale illustrating the plant as a whole, and Fig. 3 is a foreshortened perspective view of a single floret.

The exposed portion of the plant is herbaceous, generally upright with dense and compact foliage. It grows to about eighteen inches in height on the average and has a spread of about twelve inches, thus being below average in size for the Kniphofia. The growth is very vigorous and the plant multiplies rapidly.

A striking characteristic of the plant is that it comprises numerous small clones or crowns, each of which, in season, produces a flower spike. Ordinarily, in Kniphofiae, a two year old plant produces two to four clones, each having one flower spike, these crowns being fairly large, bulky and rather coarse. The present plant at two years of age produces from twelve to twenty very small and compact crowns, each of which produces a flower spike in due season, so that, for a given size plant, the present Kniphofia produces from three to five times as many flower spikes as prior Kniphofiae. Each crown readily reproduces another many crowned plant so that propagation and multiplication of the variety can be effected easily.

Other distinguishing characteristics of the plant are the recurvancy and drooping grass-like appearance of the leaves which are abundant and relatively thin and narrow, closely packed at the base of the plant, generally upright to their midportions and recurvant so as to extend outwardly and droop at their extremities. They are darker than usual for Kniphofia, being Garland Green, comparable to Maerz and Paul Plate No. 22–H–7 on the upper surface, and tipped with Winter Leaf, comparable to Maerz and Paul Plate No. 15–A–8. The color is relatively uniform. The leaves are from .2 to .32 inch across and are from fourteen to twenty-one inches long, averaging about sixteen inches. They are very narrow and generally small for Kniphofiae. The leaves are thicker and relatively stiff toward the base of the plant but are very thin and narrow above the base. They terminate in long narrow and extremely sharp points. They have smooth upper faces and closely spaced minute teeth or spines along their margins. The leaves persist excellently on the plant and their narrowness and graceful drooping and grass-like appearance are distinguishing characteristics. Near their bases the leaves are generally V-shaped in cross section, this cross section assuming more the shape of a three-pointed star progressively from the base toward the termini.

The flower stalks grow upright from the base and though of relatively small diameter are very tough and support the flower spike well and in upright position. They are strong enough to resist relatively heavy winds. They are from two and one half to three and one-half feet in length and are from .25 to .32 inch in diameter near the base, thus being of relatively small diameter than the flower stalks of most Kniphofiae. Both the leaves and flower stalks are exceedingly uniform for a given plant or for a number of plants of the same age under the same growing conditions. The color of the smaller stems and stems when bearing buds is comparable to Maerz and Paul Plate No. 13–L–6, and of the larger stems and those bearing flowers is Calliste Green, comparable to Maerz and Paul Plate No. 19–L–6.

The blooms are in the form of spikes of short pedicelled florets and are the usual shape except that they are more flattened at the top.

For flowering conditions, sun with a southern exposure or a relatively hot, dry, well drained location are preferred although the plant flowers well in ordinary garden soil. The plant, however, does not survive in the shade.

The blooming period begins the last week in June and continues through the first three weeks in July, and during this period the plant blooms continuously. The blooms persist well both in cut and uncut flowers.

The buds are produced in relatively small spikes of generally conical or pyramidal shape which are borne upright on the stalks. The color of the small buds is generally green with a noticeable pink, the general tonality being comparable to Maerz and Paul Plate No. 13–L–6. The large buds are colored almost Tigerlily, comparable to Maerz and Paul Plate No. 1–G–11.

The florets forming the spike have very short pedicels which support the florets in a generally horizontal or downward sloping position forming a very compact and solid head or spike. The spikes begin blooming at the base and the blooming progresses very rapidly upwardly so that the spikes are in full bloom over the entire extent for most of the blooming period and persist in this condition for a long period. One spike is borne on each clone or crown so that on a two year old plant fifteen to twenty spikes are in bloom concurrently, even though the plant is very small and compact.

Though the stalks are relatively short for Kniphofiae, their length varies with the richness of the soil and the moisture but they are very consistent for any given plant in a given location or group of plants of the same age in a given location.

The spikes are from four and one half to five inches long and about two inches across at the point of largest diameter.

The general tonallity of the exterior of the tubes and petals of each floret is comparable to Maerz and Paul Plate No. 1–K–11, this varying in some instance to a color, comparable to 1–L–11 and to 1–I–10. The florets are striped with a pink somewhat deeper than the general tonallity and the space between the stripes is somewhat lighter than the general tonallity. The stripe corresponds in number to the petals and each extends from the outermost margin of the petal along the midportion of the petal to the base of the tube in a straight line. On the outer surface of each tube, these stripes are also clearly observable when the floret is viewed closely but at a short distance they impart a general tonallity to the entire tube and floret which is close to the color of the stripes themselves, and, in turn, impart this general tonallity to the entire spike which is of substantially the same color throughout its entire length. The color is very intense generally and noticeably changes in intensity and brilliance when viewed from different angles; for example, the intensity increases with an apparent changing of hue when the spikes are viewed in the direct rays of the sun and decreases noticeably with a darkening in hue when viewed from the side opposite from the sun. The color of the florets remains substantially constant throughout the blooming period and when fading begins, the general color of the spikes may be said to fade pleasantly so that it does not have an unattractive appearance.

The individual florets are trumpet-shaped with a tube about three sixteenths of an inch in diameter though tapering from about the longitudinal midportion toward the base. The diameter of the open end of a floret is about seven sixteenths of an inch and the florets are about one inch long. Each floret is trumpet-like in shape and ends in a six-pointed star with a definite alternating arrangement of shape and color as illustrated in Fig. 3, wherein the No. 1 points of the star are wider and more rounded than the No. 2 points. The No. 1 points have a color which is almost an Opera Pink comparable to Maerz and Paul Chart No. 1–A–8. The No. 2 points of the star are sharper and more pointed with a color between a Safrano Pink and Pink Coral, being comparable to Maerz and Paul Chart No. 1–D–9. Each floret has very light yellow or yellowish green stamens with dark brown anthers, slightly dusted with Spanish Yellow pollen, comparable to Maerz and Paul Plate No. 10–L–7.

These dimensions of the individual florets, the number of florets on a spike and consequent size of the spike, the consistency of color and size, both of spikes and florets on a given plant, the uniform length and size of stalks and the like are exceptional, the variations being so slight as to be negligible and unnoticeable for a given plant or group of plants of the same age under the same growing conditions.

The characteristics which distinguish the plant from other Kniphofiae are the extreme floriferousness of the plant due to the large number of small and compact crowns or clones; the thin relatively slender stems of uniform length which make the plant desirable for cutting; the flower spikes which are in bloom over their entire length at the same time; the extraordinary color of the florets which is a self-color hue instead of bicolor and its consistency for plants in the same location and, correlatively, the general tonallity of the spikes; the thinness, compactness, and graceful shape of the individual leaves and their grass-like appearance in the plant; the large number of small and compact clones or crowns in a relatively small plant; and the ability to be forced under greenhouse conditions which make it highly advantageous for greenhouses and florists uses, where space is at a premium, particularly because a large number of spikes can be obtained from a relatively small plant.

Having now fully shown and described my new Kniphofia, and the mode of its production, what I claim and desire to secure by Letters Patent of the United States is:

The variety of Kniphofia, or Tritoma, herein shown and described, characterized by the small size and compactness of the plant, the extremely large number of small, flower producing crowns; the grass-like, drooping appearance of the leaves; the uniformity of its growth and of its flower spikes in a given location; the brilliant and consistent unusual coloring of its flower spikes; its extreme floriferousness; and its ability to be forced.

JOHN J. GRULLEMANS.